United States Patent [19]

Hakamatsuka et al.

[11] Patent Number: 4,747,876

[45] Date of Patent: May 31, 1988

[54] DENTAL CROWN MATERIAL

[75] Inventors: Yasuharu Hakamatsuka; Kazuhiro Watanabe, both of Hachioji, Japan

[73] Assignee: Olympus Optical Co., Ltd., Tokyo, Japan

[21] Appl. No.: 907,587

[22] Filed: Sep. 15, 1986

[30] Foreign Application Priority Data

Sep. 21, 1985 [JP] Japan ................. 60-209590

[51] Int. Cl.$^4$ .................. C03C 10/16; C09K 3/00
[52] U.S. Cl. ............................... 106/35; 65/33; 433/218; 433/222.1; 433/223; 501/3; 501/7; 501/57
[58] Field of Search ............... 106/35; 433/218, 222.1, 433/223; 501/3, 7, 57; 65/33

[56] References Cited

U.S. PATENT DOCUMENTS 3,997,352 12/1976 Beall ........................... 501/57
4,431,451 2/1984 Mabie et al. ................ 501/12
4,652,312 3/1987 Grossman et al. ........... 501/3

FOREIGN PATENT DOCUMENTS 247589  9/1962  Australia ................. 501/3
3532003 9/1962  Japan .
51-73019 6/1976  Japan .

Primary Examiner—Robert Wax
Attorney, Agent, or Firm—Frishauf, Holtz, Goodman & Woodward

[57] ABSTRACT

A dental crown formed of a dental crown material comprising crystallized glass containing 40 to 45% by weight of $SiO_2$, 11 to 15% by weight of $Al_2O_3$, 16 to 23% by weight of MgO, 6.5 to 8% by weight of F, 4.0 to 7.0% by weight of $Na_2O$, 5 to 9% by weight of $Li_2O$, not more than 1% by weight of $TiO_2$, 2 to 4% by weight of $ZrO_2$, and at least one oxide selected from the group consisting of $Fe_2O_3$, MnO, $CeO_2$ and NiO, and having a bending strength of at least 2000 $Kg/cm^2$.

11 Claims, 1 Drawing Sheet

DENTAL CROWN MATERIAL

BACKGROUND OF THE INVENTION

1. Field of the Invention

The present invention relates to a dental crown material and a dental crown used for dental treatment.

2. Description of the Prior Art

Conventionally, an alloy material such as a silver-palladium alloy, a nickel-chromium alloy and a cobalt-chromium alloy, and a metal material in which a ceramic material is fused, are used as dental crown materials. The alloy material is conveniently formed into a dental crown by a lost wax process.

When the alloy material is used in the oral cavity of a patient for a long period of time, however, a toxic metal element such as chromium, cobalt, or cadmium may elute from the alloy and be accumulated in the patient's body. In addition, since the alloy material has a high thermal conductivity and thus the difference in thermal conductivity between a crown made by the alloy material and a natural tooth is large, when the patient eats food having a large temperature difference from the body temperature, he may often experience discomfort.

Since a crown formed by a metal material containing a fused ceramic material is too hard, it creates wear on the opposing tooth. Also, its color is not natural compared to that of a natural tooth, and its moldability is poor.

SUMMARY OF THE INVENTION

It is, therefore, an object of the present invention to provide a dental crown which has sufficient moldability similar to that of an alloy material, has thermal conductivity close to that of a natural tooth, and has good mechanical strength.

A dental crown of the present invention is made of crystallized glass containing 40 to 45% by weight of $SiO_2$, 11 to 15% by weight of $Al_2O_3$, 16 to 23% by weight of MgO, 6.5 to 8% by weight of F, 4.0 to 7.0% by weight of $Na_2O$, 5 to 9% by weight of $Li_2O$, 1% by weight or less of $TiO_2$, and 2 to 4% by weight of $ZrO_2$.

DESCRIPTION OF THE PREFERRED EMBODIMENTS

As described above, the dental crown according to the present invention is made of crystallized glass containing 40 to 45% by weight of $SiO_2$, 11 to 15% by weight of $A_2O_3$, 16 to 23% by weight of MgO, 6.5 to 8% by weight of F, 4.0 to 7.0% by weight of $Na_2O$, 5 to 9% by weight of $Li_2O$, 1% by weight or less of $TiO_2$, and 2 to 4% by weight of $ZrO_2$.

Upon a heat treatment to be described later, $SiO_2$, $Al_2O_3$, MgO, F, $Na_2O$, and $Li_2O$ precipitate a Na·Mg·$(Si_3AlO_{10})F_2$ crystal phase (mica) phase having a good machinability, and an $Li_2O·Al_2O_3·2SiO_2$ crystal phase ($\beta$-eucryptite phase) and an $Li_2O·Al_2O_3·4SiO_2$ crystal phase ($\beta$-spodumene phase) both having a good mechanical strength. $TiO_2$ and $ZrO_2$ control crystal growth and improve the mechanical strength of the crown.

The dental crown material of the present invention can contain, in addition to the above components, 1 to 7% by weight of ZnO in order to decrease the melt viscosity and to facilitate casting of the material into a mold. Furthermore, the crown material of the present invention can contain up to 0.5% by weight of $Fe_2O_3$, up to 0.05% by weight of MnO, up to 0.1% by weight of NiO and/or up to 0.1% by weight of $CeO_2$ in order to control the color.

Figure 1A:
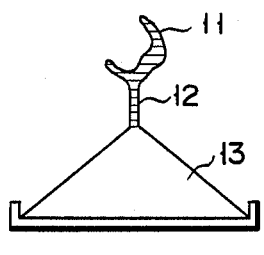
FIGS. 1A to 1D are schematic views for illustrating a method of fabricating a crown of the present invention in accordance with its steps.
Figure 1B:
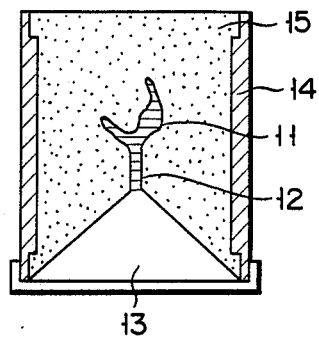
Figure 1C:
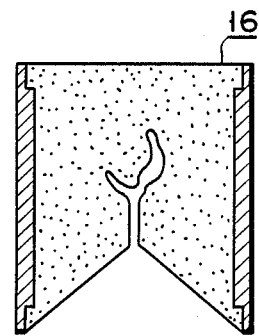
Figure 1D:
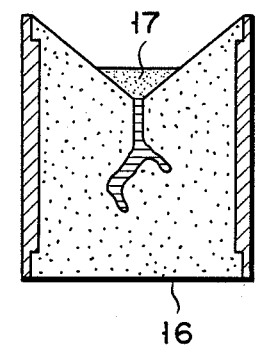

When a crystallized glass dental crown is prepared from the crown material of the present invention, a known lost wax process is employed. More specifically, as shown in FIG. 1A, a wax is coated on a decayed tooth to obtain a mold therefor, thus preparing the wax pattern 11. Pattern 11 is provided with sprue line 12 made of wax and is fixed on conical sprue base 13 therethrough. Subsequently, as shown in FIG. 1B, base 13 is surrounded by casting ring 14. Cristobalite- or quartz-type investing material 15 is filled in casting ring 14 and is hardened. Then, as shown in FIG. 1C, pattern 11 and sprue line 12 are heated and removed to provide lost wax casting mold 16. As shown in FIG. 1D, dental crown material 17 of the present invention is melted at 1350° to 1400° C. and casted into casting mold 16 under pressure or is subjected to a centrifugal force by a centrifugal casting machine. When the dental crown material is hardened, it is removed from mold 16 and is crystallized by heating at 700° to 750° C. for 2 hours and then raising the temperature to 900°~950° C. for 1 hour. The above-described mica crystal phase, the $\beta$-eucryptite phase, and the $\beta$-spodumene crystal phase are formed within the heating time, thereby providing a uniform, dense crystal texture. It is preferable that the mica crystal phase, $\beta$-eucryptite crystal phase, and $\beta$-spodumene crystal phase are precipitated in a ratio of 5 to 30% by weight, 0 to 10% by weight, and 5 to 30% by weight, respectively.

When heat treatment is completed in this manner, a portion of the casted body corresponding to sprue line 12 is removed by machining, thereby obtaining a dental crown of the present invention.

Since the dental crown material of the present invention does not react with cristobalite or quartz as the investing material, a heat treatment for glass crystallization can be performed within the lost wax casting mold 16, and the surface of the obtained crown can be smooth.

The present invention will be described by way of its Example.

EXAMPLE

In this example, the quartz- and cristobalite-type materials shown in Table 1 were used as the investing materials, and the dental crown materials having the compositions (parts by weight) shown in Table 2 were casted therein.

TABLE 1

| | Quartz investing material | | | Cristobalite investing material | | |
|---|---|---|---|---|---|---|
| | A | B | C | D | E | F |
| Water-mixing ratio | 0.30 | 0.32 | 0.25 | 0.36 | 0.32 | 0.38 to 0.42 |
| Hardening time (min.) | 11 | 10 | 12 | 12 | 10 | 10 to 14 |
| Hardening expansion (%) | 0.35 | 0.35 | 0.26 | 0.33 | 0.40 | 0.20 to 0.25 |
| Thermal expansion (%) | 0.82 | 0.90 | 1.08 | 1.47 | 1.41 | 1.27 |
| Total | 1.17 | 1.25 | 1.34 | 1.80 | 1.81 | 1.47 to 1.52 |

TABLE 1-continued

| | Quartz investing material | | | Cristobalite investing material | | |
|---|---|---|---|---|---|---|
| | A | B | C | D | E | F |
| expansion (%) | | | | | | |

TABLE 2

| Composition | Sample | | | | |
|---|---|---|---|---|---|
| | No. 1 | No. 2 | No. 3 | No. 4 | No. 5 |
| $SiO_2$ | 43.0 | 42.0 | 41.1 | 42.0 | 47.2 |
| $Al_2O_3$ | 11.0 | 12.0 | 14.3 | 12.0 | 16.7 |
| MgO | 17.0 | 20.0 | 22.6 | 18.0 | 14.5 |
| ZnO | 1.0 | 7.0 | — | 3.0 | — |
| $Na_2O$ | 4.0 | 4.4 | 7.0 | 4.4 | — |
| $Li_2O$ | 5.6 | 8.1 | 8.1 | 8.1 | — |
| TiO | — | — | — | 1.0 | — |
| $ZrO_2$ | — | — | — | 2.0 | — |
| $Fe_2O_3$ | — | — | — | 0.1 | — |
| MnO | — | — | — | 0.01 | — |
| NiO | — | — | — | 0.05 | — |
| $CeO_2$ | — | — | — | 0.1 | — |
| F | 6.9 | 6.5 | 6.9 | 7.5 | 6.3 |
| $B_2O_3$ | — | — | — | — | 8.5 |
| $K_2O$ | — | — | — | — | 9.5 |

In Table 2, sample No. 4 is a product according to the present invention, and sample No. 5 is a commercially available material having a good machinability and in which mica crystals are precipitated. The raw materials having the compositions shown in Table 2 were dissolved at a temperature of 1,200° C. for 50 minutes and then heated at a temperature of 1,400° C. for 1 hour. Samples Nos. 1, 2, and 4, to which ZnO had been added, had a lower viscosity than samples Nos. 3 and 5, to which ZnO had not been added, and could be cast easily. The molten glass was cast into a casting mold obtained using the investing material (shown in Table 1) heated to a temperature of 600° C. and was cooled gradually. After gradual cooling, the glass was heated to a temperature of 750° C. over 1 hour, was left to stand for 3 hours at that temperature, was heated to a temperature of 950° C. over 1 hour, and was cooled.

Samples Nos. 1 to 4 obtained in this manner were subjected to testing for bending strength and Vickers hardness. The bending strengths of samples Nos. 1 to 4 were larger than that (1,000 kg/cm$^2$) of sample No. 5 and fell within the range of 2,000 and 2,700 kg/cm$^2$. The Vickers hardnesses (Hv) of samples Nos. 1 to 4 fell within the range of 340 to 400, which is close to that of a natural tooth. Note that the bending strengths of the glasses of samples Nos. 1 to 4 before heat treatment were 600 to 700 kg/cm$^2$ and the Vickers hardnesses (Hv) thereof were near 600.

The molded products which were crystallized by the heat treatment were subjected to X-ray analysis. The analysis results indicate that Na·Mg$_3$·(Si$_3$AlO$_{10}$)F$_2$ crystals (mica), Li$_2$O·Al$_2$O$_3$·2SiO$_2$ crystals (β-eucryptite), and Li$_2$O·Al$_2$O$_3$·4SiO$_2$ crystals (β-spodumene) were precipitated.

Table 3 shows comparison results of the various characteristics of the molded products after thermal treatment. o and Δ in Table 3 indicate good and poor, respectively, which were determined in accordance with the following criteria. Moldability of a product was determined in accordance with whether or not the product had a sufficient viscosity at 1,400° C. Crystallization property of a product was determined in accordance with whether or not the product had a crystallinity exceeding 50% when 3 hours for crystallization had elapsed. Machinability of a product was determined in accordance with the time required for machining the product using a machining hand piece currently employed in the field of dental treatment. Hardness of a product was determined whether it was equivalent to 340 to 400 in Vickers hardness (Hv). Bending strength of a product was determined in accordance with whether it exceeds 1,500 kg/cm$^2$. Appearance of a product was determined whether its color is close to that of a natural human tooth. Chemical resistance of a product was determined in accordance with whether it corresponded to 1 or more defined by the Japan Optical Glass Industries' Association Standard. Note that the above molded products are stable and nontoxic with respect to a living body since the eluted substance from the product, if any, is alkali ions or oxyanions.

TABLE 3

| | No. 1 | No. 2 | No. 3 | No. 4 | No. 5 |
|---|---|---|---|---|---|
| Moldability | o-Δ | o | Δ | o | Δ |
| Crystallization Property | Δ | o | o | o | o-Δ |
| Machinability | o | o | o | o | o |
| Hardness | o | o | o | o | o-Δ |
| Bending strength | o | o | o | o | Δ |
| Appearance | Δ | Δ | Δ | o | Δ |
| Chemical resistance | o | o | o | o | o |

As shown in Table 3, it was found that the materials of samples Nos. 1 to 4 exhibited the characteristics equivalent to or better than those of the material of commercially available sample No. 5. Also, the material of sample No. 5 had a thermal conductivity close to that of a natural human tooth compared to a metal alloy, while the materials of samples Nos. 1 to 4 exhibited thermal conductivities substantially the same as that of sample No. 5.

According to the present invention, a dental crown material close to a natural human tooth is obtained which has a moldability similar to that of a conventional metallic dental crown material, a machinability as good as that of a metal, hardness and mechanical strength equivalent to or better than those of a natural human tooth, and thermal conductivity and appearance better than those of a conventional crown material. Since the material of the present invention is an oxide, it has a good affinity with respect to a living body.

What is claimed is:

1. A dental crown formed of a dental crown material comprising crystallized glass containing 40 to 45% by weight of SiO$_2$, 11 to 15% by weight of Al$_2$O$_3$, 16 to 23% by weight of MgO, 6.5 to 8% by weight of F, 4.0 to 7.0% by weight of Na$_2$O, 5 to 9% by weight of Li$_2$O, not more than 1% by weight of TiO$_2$, 2 to 4% by weight of ZrO$_2$, and at least one oxide selected from the group consisting of Fe$_2$O$_3$, MnO, CeO$_2$ and NiO, and having a bending strength of at least 2000 Kg/cm$^2$.

2. The crown according to claim 1 wherein the crystallized glass contains a mica crystal phase, a β-eucryptite crystal phase, and a β-spodumene crystal phase.

3. The crown according to claim 1 wherein Fe$_2$O$_3$ is in an amount up to 0.5%, said MnO is in an amount up to 0.05%, said NiO is in an amount up to 0.1% and said CeO$_2$ is in an amount up to 0.1%.

4. The crown according to claim 2 wherein Fe$_2$O$_3$ is in an amount up to 0.5%, said MnO is in an amount up to 0.05%, said NiO is in an amount up to 0.1% and said CeO$_2$ is in amount up to 0.1%.

5. The crown according to claim 4, wherein the crown material further comprises 1 to 7% by weight of ZnO.

6. The crown according to claim 1 which contains $Fe_2O_3$, MnO, NiO and $CeO_2$.

7. The crown according to claim 5 which contains $Fe_2O_3$, MnO, NiO and $CeO_2$.

8. The crown according to claim 1 which contains 0.1% $Fe_2O_3$, 0.01% MnO, 0.005% NiO and 0.1% $Ce_2O_2$.

9. The crown according to claim 5 which contains 0.1% $Fe_2O_3$, 0.1% MnO, 0.005% NiO and 0.1% $CeO_2$.

10. The crown according to claim 8 which contains 42% $SiO_2$, 12% $Al_2O_3$, 18% MgO, 3% ZnO, 4.4% $Na_2O$, 8.1% $Li_2O$, 1% $TiO_2$, 2% $ZrO_2$ and 7.5% F.

11. The crown according to claim 9 which contains 42% $SiO_2$, 12% $Al_2O_3$, 18% MgO, 3% ZnO, 4.4% $Na_2O$, 8.1% $Li_2O$, 1% $TiO_2$, 2% $ZrO_2$ and 7.5% F.

* * * * *